(12) United States Patent
Anderson et al.

(10) Patent No.: US 10,639,030 B2
(45) Date of Patent: May 5, 2020

(54) SUTURING DEVICE HAVING ADJUSTABLE DISTAL END

(71) Applicant: Dura Tap LLC, Wayne, PA (US)

(72) Inventors: David Greg Anderson, Villanova, PA (US); Mark F. Kurd, Wayne, PA (US); Jay Tapper, Wayne, PA (US); Jens Johnson, Austin, TX (US)

(73) Assignee: Durastat LLC, Wayne, PA (US)

( * ) Notice: Subject to any disclaimer, the term of this patent is extended or adjusted under 35 U.S.C. 154(b) by 205 days.

(21) Appl. No.: 15/832,917

(22) Filed: Dec. 6, 2017

(65) Prior Publication Data
US 2019/0167255 A1 Jun. 6, 2019

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0482* (2013.01); *A61B 17/06061* (2013.01); *A61B 2017/003* (2013.01); *A61B 2017/00323* (2013.01); *A61B 2017/00991* (2013.01); *A61B 2017/06042* (2013.01); *A61B 2017/06095* (2013.01)

(58) Field of Classification Search
CPC ...... A61F 2/243; A61F 2/2418; A61F 2/2409; A61F 2/2427; A61F 2/2436; A61F 2/2439; A61F 2/2451; A61F 2/2457; A61F 2/2466
See application file for complete search history.

(56) References Cited

U.S. PATENT DOCUMENTS

| | | | | |
|---|---|---|---|---|
| 2006/0041263 | A1* | 2/2006 | Chu | A61B 17/0469 606/144 |
| 2008/0109015 | A1* | 5/2008 | Chu | A61B 17/0469 606/139 |
| 2013/0211513 | A1* | 8/2013 | Rourke | A61F 2/2466 623/2.37 |

* cited by examiner

*Primary Examiner* — Tuan V Nguyen
(74) *Attorney, Agent, or Firm* — Rankin, Hill & Clark LLP

(57) ABSTRACT

A suturing device includes an elongate body, a needle, an actuator, and a needle holder. The actuator interacts with the elongate body and is operable between a first operating position and a second operating position. The actuator is configured such that movement of the actuator from the first operating position toward the second operating position moves the needle in an advance direction. The needle holder extends away from a distal end portion or is provided as part of the distal end portion of the elongate body. The needle holder defines a needle passage and a distal opening. The needle is positioned in the needle passage when the actuator is in the first operating position. The needle holder is configured to move with respect to the elongate body to change the location of the distal opening with respect to the elongate body.

6 Claims, 13 Drawing Sheets

SUTURING DEVICE HAVING ADJUSTABLE DISTAL END

BACKGROUND

The present disclosure relates generally to surgery and the placement of sutures, and more particularly, to devices and methods for the suture repair of tissue.

Surgical closure techniques using sutures is one approach to tissue repair. In some instances, however, these techniques can be difficult to execute due to anatomic constraints, obstruction of visualization by blood or other bodily fluids, and the proximity to nerve rootlets. In some instances, these challenges can be further complicated when using minimally invasive techniques such as, for example, a tubular retractor. Traditional tools and devices can be limited and, in some instances, lack maneuverability to avoid obstructions and/or to enable adequate passage of the needle and suture through the tissue

SUMMARY

In view of the foregoing a suturing device includes an elongate body, a needle, an actuator, and a needle holder. The elongate body includes a proximal end portion and a distal end portion. The needle includes a first end, which is pointed, and a second end, which is opposite the first end. The actuator interacts with the elongate body and is operable between a first operating position and a second operating position. The actuator is configured such that movement of the actuator from the first operating position toward the second operating position moves the needle in an advance direction. The needle holder extends away from the distal end portion or is provided as part of the distal end portion of the elongate body. The needle holder defines a needle passage and a distal opening. The needle is positioned in the needle passage when the actuator is in the first operating position. The needle passes through the distal opening when moving in the advance direction. The needle holder is configured to move with respect to the elongate body to change the location of the distal opening with respect to the elongate body.

DETAILED DESCRIPTION

Figure 1:
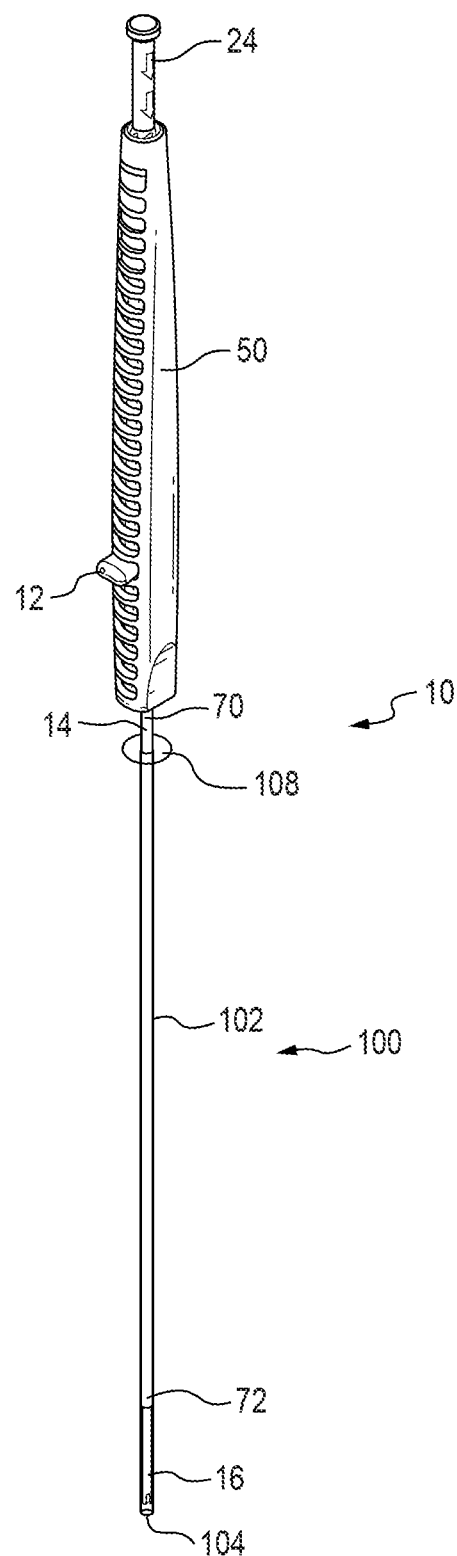
FIG. 1 is a perspective view of a suturing device including a needle holder having a distal opening and a distal opening positioning mechanism in a first operating state.
Figure 4:
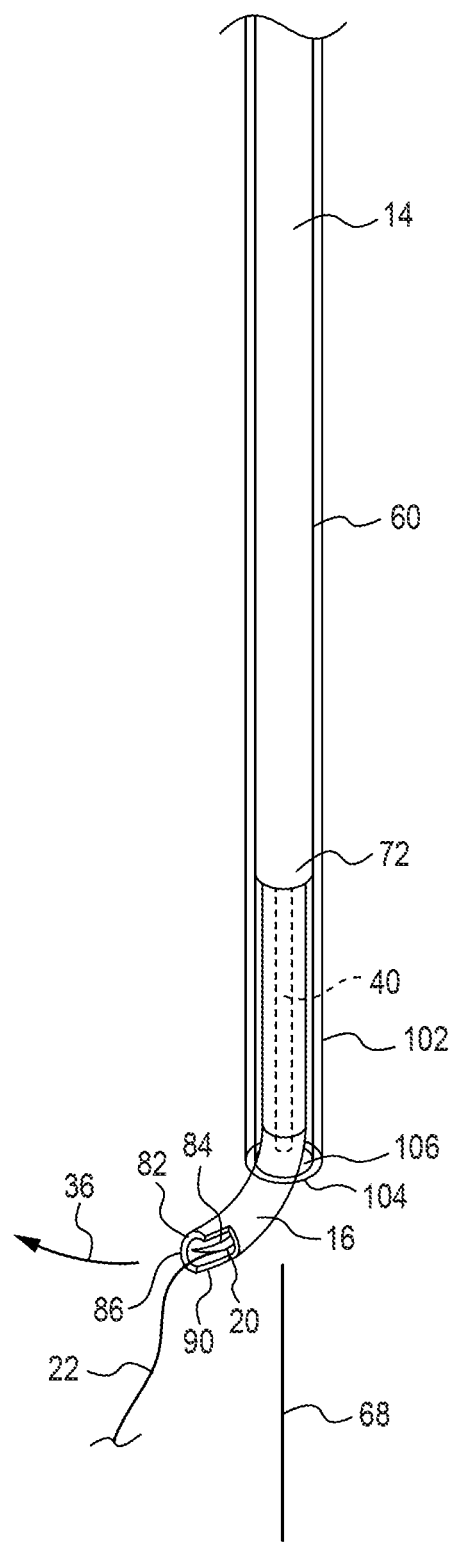
FIG. 4 is perspective view of a distal end portion of the suturing device depicted in FIG. 3.

FIG. 1 depicts an example of a suturing device 10 that is useful to suture tears in tissue and that can be used in many different types of surgical procedures. The suturing device 10 generally includes an actuator having a button 12, an elongate body 14, and a needle holder 16. The suturing device 10 is particularly useful during a minimally invasive surgical procedure that is performed through a tubular retractor or other small surgical portal to accurately locate a needle 20 and a suture 22, which are shown in FIG. 4, to facilitate passing the needle 20 through target tissue to be sutured.

The needle 20 in the illustrated embodiment is a curved needle having a first end, which is pointed, and a second end, which is opposite to the first end. The needle 20 can be similar to commercially available curved needles made from known materials. The needle 20 could also be formed from a malleable, or flexible, material such that the needle 20 could follow a curve when positioned within the needle holder 16, which can be curved, and then later straighten after exiting the needle holder 16. Both the needle holder 16 and the needle 20 can take other configurations.

The actuator, which includes the button 12 and a plunger 24, is more particularly described in U.S. application Ser. No. 15/654,878, which is incorporated by reference herein. Actuation of the actuator moves the needle 20 in an advance direction 36 with respect to the needle holder 16. The needle 20 moves from a retracted position, which is shown in FIG. 4, to a released condition in which the needle 20 is released from the needle holder 16. When in the released condition, the surgeon can grasp the needle 20, for example with forceps, and pull the needle 20 and the suture 22. The suture 22 connects with the needle 20 and extends from the second end of the needle 20. The suture 22 can be swaged to the second end of the needle 20. The suture 22 can also connect with the needle 20 in other conventional manners. The suture 22 can be acquired from known suture manufacturers.

The actuator is operable between a first operating position and a second operating position. Movement of the actuator from the first operating position toward the second operating position moves the needle 20 in the advance direction 36 with respect to the needle holder 16 thus moving the needle 20 toward the released condition in which the needle 20 is released from the needle holder 16. In the illustrated embodiment, the actuator includes a flexible section, which in the illustrated embodiment is made up of a wire 40, which can be made from nitinol. The flexible section is configured to bend within the needle holder 16 when the actuator is moved from the first operating position toward the second operating position. The other components of the actuator are described in more detail in U.S. application Ser. No. 15/654878 and will not be described herein for the sake of brevity.

The elongate body 14 connects with a handle 50 in the illustrated embodiment. The elongate body 14 in the illustrated embodiment is in the form of a cannula. The elongate body 14 has an outer surface 60, which is smooth, and defines a track (not visible in FIGS. 1-4) that receives a portion of the actuator, more particularly the wire 40 in the illustrated embodiment. As described above, the elongate body 14 is a cannula and the track is a lumen that receives the wire 40 of the actuator. The track need not encircle the wire 40, but could be U-shaped. In the depicted embodiments, the elongate body 14 is circular in a cross section taken normal to the longest dimension of the elongate body 14, however, the elongate body 14 could take alternative configurations, such as polygonal or U-shaped.

The elongate body 14 extends straight along a longitudinal axis 68 in the illustrated embodiment; however, the elongate body 14 could take alternative configurations, such as a bayonet configuration. The elongate body 14 includes the proximal end portion 70 and a distal end portion 72. The proximal end portion 70 connects with the handle 50. In the illustrated embodiment, the needle holder 16 is received in and connected with the elongate body 14 and extends away from the distal end portion 72. Alternatively, the needle holder 16 can be provided as part of the distal end portion 72 of the elongate body 14. The elongate body 14 is made from a rigid metal material; however, if desired at least a portion of the elongate body 14 may be made from a malleable or flexible material to allow the surgeon to bend at least a portion of the elongate body 14 into a desirable configuration for insertion into an animal body during a surgical procedure. In the illustrated embodiment, an outer diameter of the elongate body 14 is constant between the proximal end portion 70 and the distal end portion 72. The outer diameter can be less than 3.5 mm, which provides a very slim device to enhance the line of sight for a surgeon during the surgical procedure.

The proximal end portion 70 of the elongate body 14 is received in the handle 50. The elongate body 14 and the needle holder 16 can rotatable with respect to the handle 50 about a rotational axis, which in the illustrated embodiment is coaxial with the longitudinal axis 68; however, rotation of the elongate body 14 and the needle holder 16 with respect to the handle 50 requires a greater amount of force to be applied on the elongate body 14 or needle holder 16 than the force that is typically applied to the elongate body 14 or the needle holder 16 while a surgeon is using the suturing device 10 during a suturing procedure.

Figure 2:
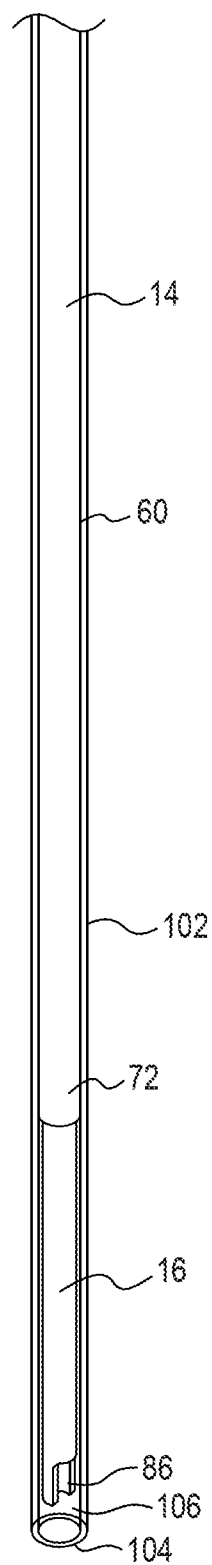
FIG. 2 is perspective view of a distal end portion of the suturing device depicted in FIG. 1.
Figure 3:
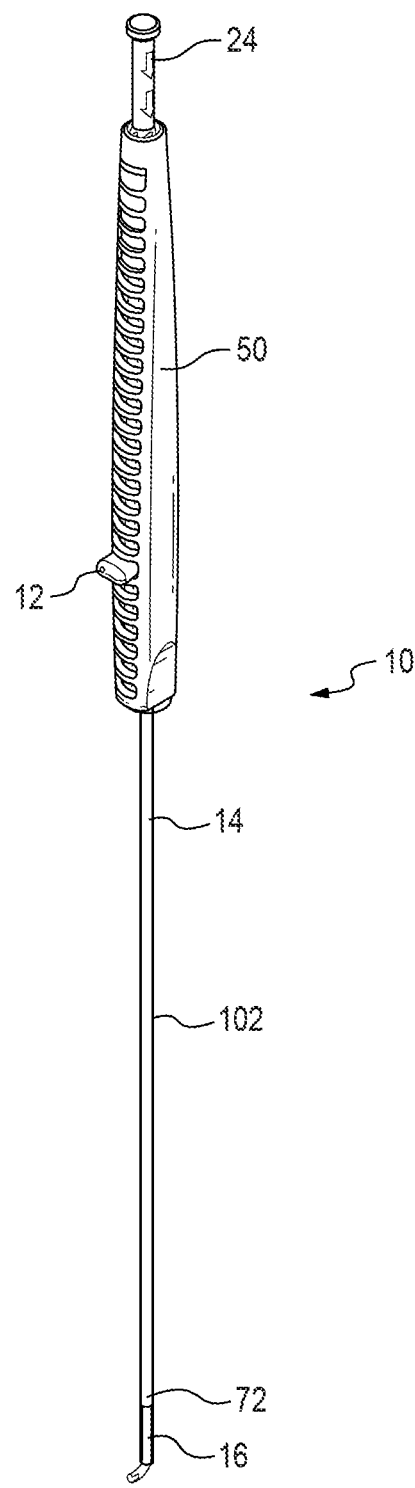
FIG. 3 is a perspective view of the suturing device depicted in FIG. 1 with the distal opening positioning mechanism in a second operating state.

The needle holder 16 extends away from the distal end portion 72 or is provided as part of the distal end portion 72 of the elongate body 14. In the illustrated embodiment, the needle holder 16 is a hollow tubular member. For the embodiment depicted in FIGS. 1-4, the needle holder 16 is made from a shape memory material that returns to a pre-deformed shape, which is shown in FIGS. 3 and 4, after a force has been removed. For the needle holder 16 depicted in FIGS. 1-4, in the pre-deformed shape the needle holder 16 generally follows a constant radius such that the suturing device 10 can have J-hook configuration at a distal end thereof after the needle holder returns to the pre-deformed shape.

With reference to FIG. 4, the needle holder 16 includes a distal-most tip 82. The needle holder 16 defines a needle passage 84 that is in communication with the track of the elongate body 14 and a distal opening 86. The distal opening 86 is offset from the longitudinal axis 68 in a forward direction. In the embodiment depicted in FIGS. 1-4, at least a portion of the suture 22 extends along the needle passage 84 from the second end of the needle 20 toward the distal opening 86 between the needle 20 and an inner surface of the needle holder 16 when the needle 20 is received in the needle passage 84 and the actuator is in the first operating position. The distal-most tip 82 is offset from the longitudinal axis 68 in a direction perpendicular from the longitudinal axis 68 a distance of less than 7 mm.

As more clearly seen in FIG. 4, the needle holder 16 includes a notch 90. As the needle 20 advances in the advance direction 36, the first end 30 of the needle 20 can pass through target tissue to be sutured. By providing the notch 90, the second end 32 of the needle 20 need not travel past the distal-most tip 82 of the needle holder 16 before being released from the needle holder 16. The notch 90 is depicted on the side of the needle holder 16, however, the notch 90 can be located elsewhere. By providing the notch 90, the distal opening 86 is non-circular. The distal-most tip 82 can also be rounded (see FIG. 6), which allows for the surgeon to grab or "hook" the target tissue, which is to be sutured, on an internal side thereof and indent the target tissue with the distal-most tip 82 while not catching the target tissue with the first (pointed) end 30 of the needle 20.

The needle holder 16 is configured to move with respect to the elongate body 14 to change the location of the distal opening 86 with respect to the elongate body 14. The suturing device 10 includes a distal opening positioning mechanism 100 operatively connected with the needle holder 16 and operable in different operating states to move the distal opening 86 with respect to the elongate body 14. The distal opening positioning mechanism 100 is shown in a first operating state in FIGS. 1 and 2 and a second operating state in FIGS. 3 and 4.

With reference to FIG. 1, the distal opening positioning mechanism 100 includes a movable element, which is a sleeve 102 in FIG. 1, connected with and movable with respect to the elongate body 14 and also connected with the needle holder 16. A distal end portion 104 of the sleeve 102 is positioned adjacent the distal opening 86 of the needle holder 16 when the distal opening positioning mechanism 100 is in a first operating state prior to moving the distal opening 86 with respect to the elongate body 14. The sleeve 102 depicted in FIGS. 1-4 is tubular and hollow to define a sleeve passage 106 from the distal end portion 104 to a flange 108 (FIG. 1) extending outwardly from the sleeve 102 located at or adjacent a proximal end of the sleeve 102. The flange 108 is an example of a manipulatable element provided on the sleeve 102 that is configured to be manipulated by a human hand to move the sleeve 102 with respect to the elongate body 14. The sleeve 102 is depicted as hollow between the flange 108 and the distal end portion 104, however, it can take other configurations, e.g. U-shaped or fully surrounding the elongate body 14 along only a portion of elongate body 14 to allow for the sleeve 102 to connect with the elongate body 14.

The sleeve 102 is made from a material that is more rigid than the material from which the needle holder 16 is made. As seen in FIG. 2, when in the first operating state, the sleeve 102 receives the needle holder 16 in the sleeve passage 106 and covers the distal opening 86. As mentioned above, the needle holder 16 is made from a shape memory material that returns to a pre-deformed shape, which is shown in FIGS. 3 and 4, after a force has been removed. The sleeve 102 applies this force to the needle holder 16 so that the needle holder 16 follows the shape of the sleeve passage 106 when received therein. The sleeve 102 can straighten the needle holder 16 by applying the force necessary to deform the needle holder 16 from its pre-deformed, which is curved in the illustrated embodiment.

In the first operating state, the flange 108 is offset from the handle 50. A surgeon can grasp the flange 108 and pull the flange 108 toward the handle 50 to move the distal opening positioning mechanism 100 toward the second operating position. This moves the sleeve 102 along the elongate body 14 towards the handle 50 moving the distal end portion 104 away from the distal-most tip 82 of the needle holder 16. With the sleeve 102 moved away from the distal-most tip 82 of the needle holder 16, the needle holder 16 is allowed to return to its pre-deformed shape, as shown in FIGS. 3 and 4.

Figure 5:
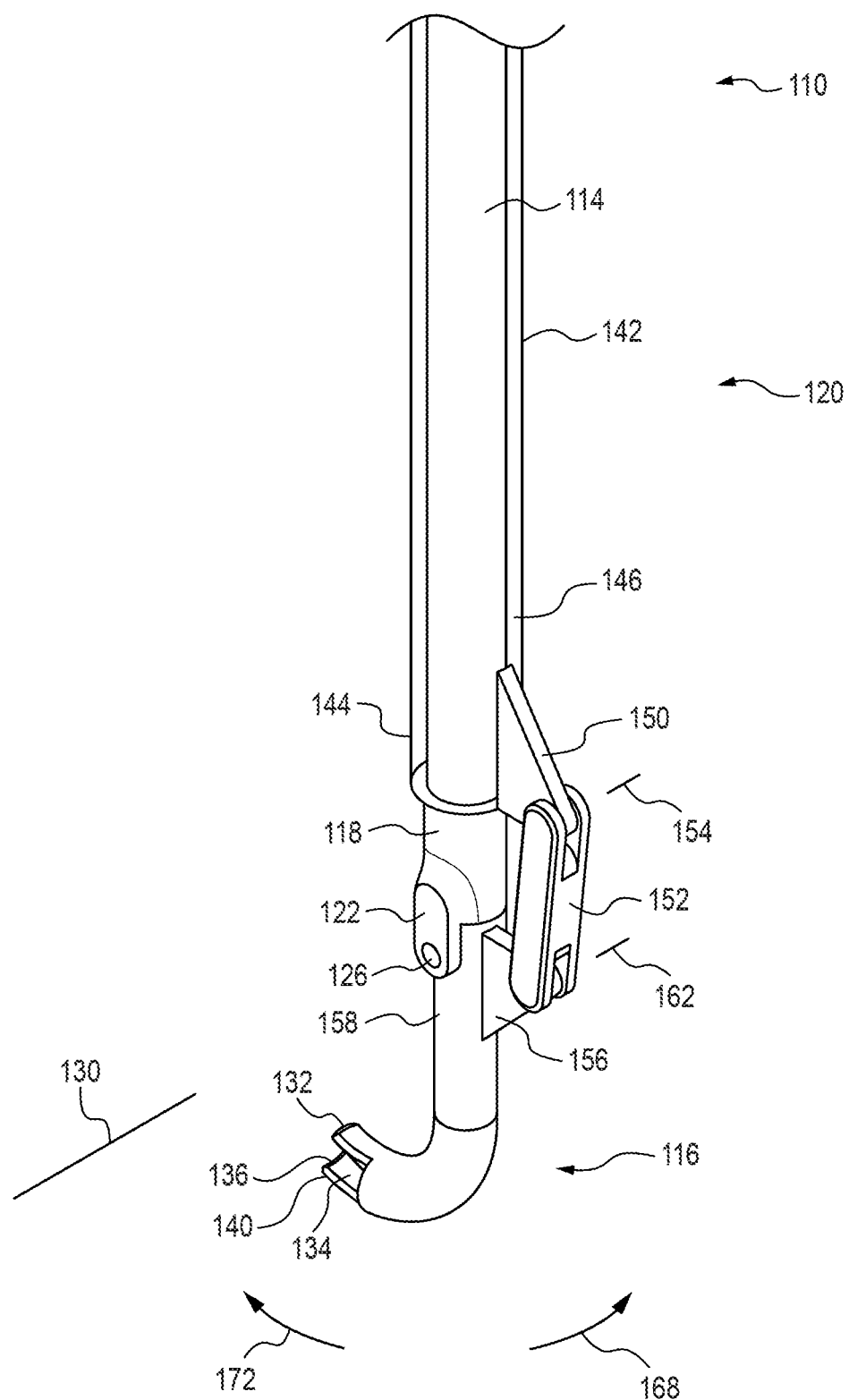
FIG. 5 is a perspective view of a distal end portion of a suturing device including an alternative needle holder having a distal opening and an alternative distal opening positioning mechanism.
Figure 6:
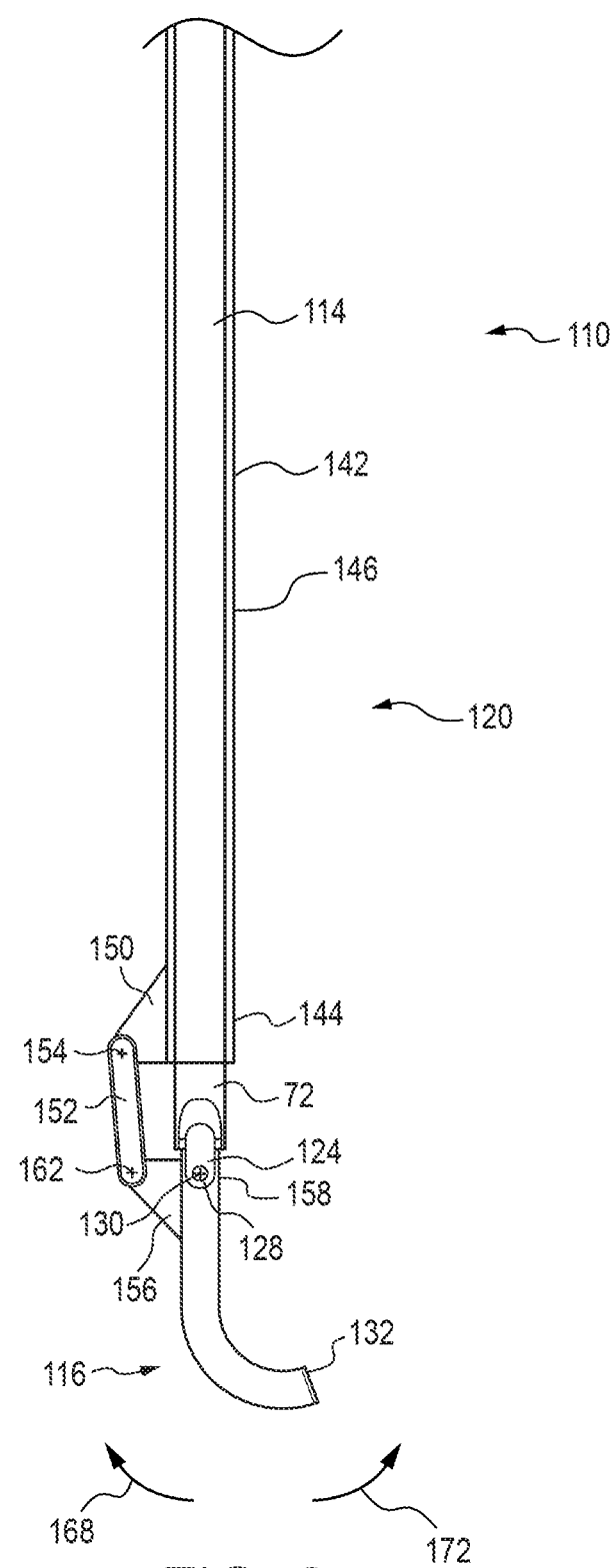
FIG. 6 is a side view of the distal end portion of the suturing device depicted in FIG. 5.

FIGS. 5 and 6 depict a distal end portion of a suturing device 110 that is similar to the suturing device 10 depicted in FIGS. 1-4, however, the suturing device 110 depicted in FIGS. 4 and 5 includes an alternative needle holder 116 and an alternative distal opening positioning mechanism 120. The suturing device 110 depicted in FIGS. 5 and 6 includes an actuator similar to the actuator described above, an elongate body 114, which is also similar to the elongate body 14 described with reference to FIGS. 1-4, and the needle holder 116. The actuator and the elongate body 114 have been described above.

The needle holder 116 extends away from a distal end portion 118 of the elongate body 114. Needle holder mounts, for example, a first needle holder mount 122 (FIG. 5) and a second needle holder mount 124 (FIG. 6), extend from the distal end portion 118 of the elongate body 114. Each needle holder mount 122, 124 receives an axle 126, 128, respectively, such that the needle holder 116 is pivotally connected with the elongate body 114 for rotation about a needle holder pivot axis 130 with respect to the elongate body 114. The needle holder 116 is similar to the needle holder 16 described above except that it is not made from a shape memory material, but is instead made from a relatively more rigid material and includes a distal-most tip 132, a needle passage 134, and a distal opening 136. A needle (not shown) but similar to the needle 20 described above, is received in the needle passage 134 along with the suture, which is similar to the suture 22 depicted in FIG. 4. The needle holder 116 also includes a notch 140, which allows the needle holder 16 to operate in a similar manner to the needle holder 16 described above when the needle holder 16 is its pre-deformed shape.

The distal opening positioning mechanism 120 depicted in FIGS. 5 and 6 includes a moveable element, which can be a sleeve 142 similar to the sleeve 102, connected with and moveable with respect to the elongate body 114 and also connected with the needle holder 116 in a manner that will be described in more detail below. The sleeve 142 includes a distal end portion 144 positioned adjacent to the needle holder 116. The sleeve 142 depicted in FIGS. 5 and 6 is tubular and hollow to define a sleeve passage 146 that receives the elongate body 114 to allow the sleeve 142 to connect with the elongate body 114. A flange (not shown) that is similar to the flange 108 can be provided at a proximal end of the sleeve 142 to provide a manipulatable element configured to be manipulated by a human hand to move the sleeve 142 with respect to the elongate body 114. Like the sleeve 102 described above, the sleeve 142 as depicted is hollow between the flange and the distal end portion 144, however, the sleeve 142 can take other configurations, e.g., U-shaped or fully surrounding the elongate body 114 along only a portion of the elongate member.

A first linkage mount 150 extends from the distal end portion 144 of the sleeve 142. The first linkage mount 150 is pivotally connected with a linkage 152 to allow for the linkage 152 to pivot about a first axis 154 with respect to the first linkage mount 150. A second linkage mount 156 extends from a proximal end portion 158 of the needle holder 116 and pivotally connects with the linkage 152. As such, the linkage 152 can pivot with respect to the second linkage mount 156 about a second axis 162.

The sleeve 142 is moveable with respect to the elongate body 114 to change the operating state of distal opening positioning mechanism 120, e.g., between a first operating state and a second operating state. Upward (per the orientation of FIGS. 5 and 6) movement of the sleeve 142 with respect to the elongate body 114 results in the needle holder 116 pivoting about the needle holder pivot axis 130 in the direction of arrow 168. Downward (per the orientation of FIGS. 5 and 6) movement of the sleeve 142 with respect to the elongate body 114 results in pivotal movement of the needle holder 116 about the needle holder pivot axis 130 in the direction of arrow 172. As such, the distal opening positioning mechanism 120 is operable in different operating states to move the distal opening 136 with respect to the elongate body 114.

Figure 7:
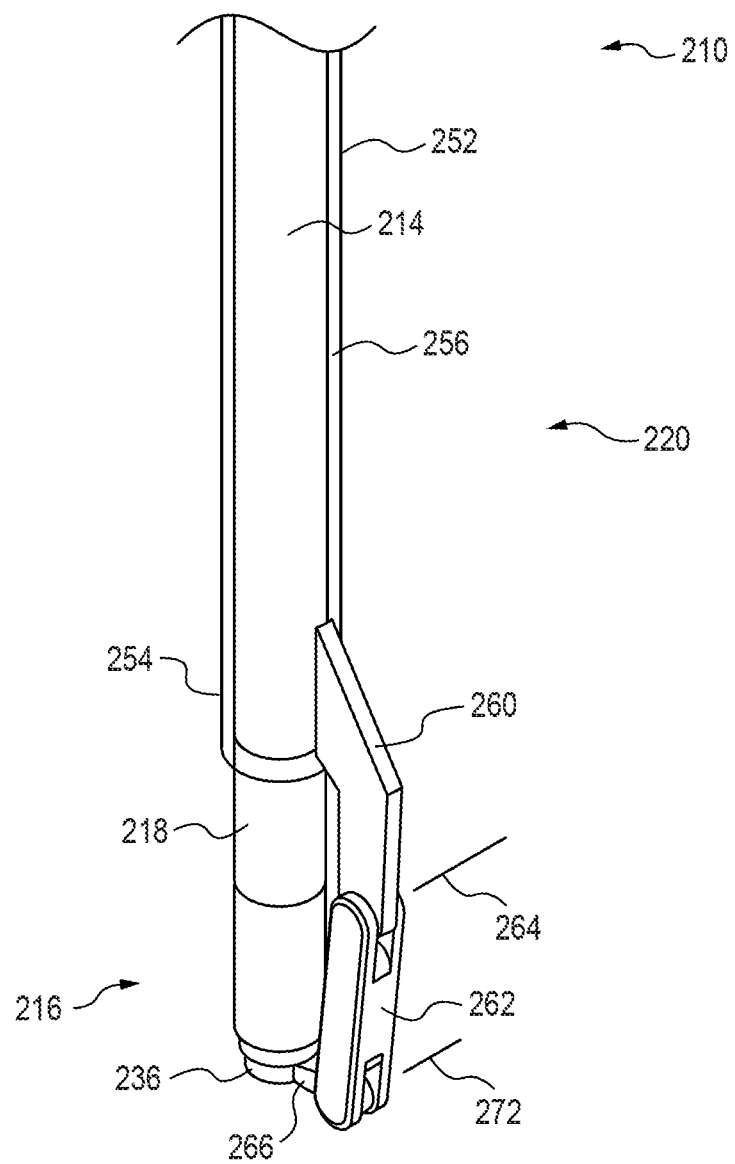
FIG. 7 is a perspective view of a distal end portion of a suturing device including another alternative needle holder having a distal opening and another alternative distal opening positioning mechanism in a first operating state.
Figure 8:
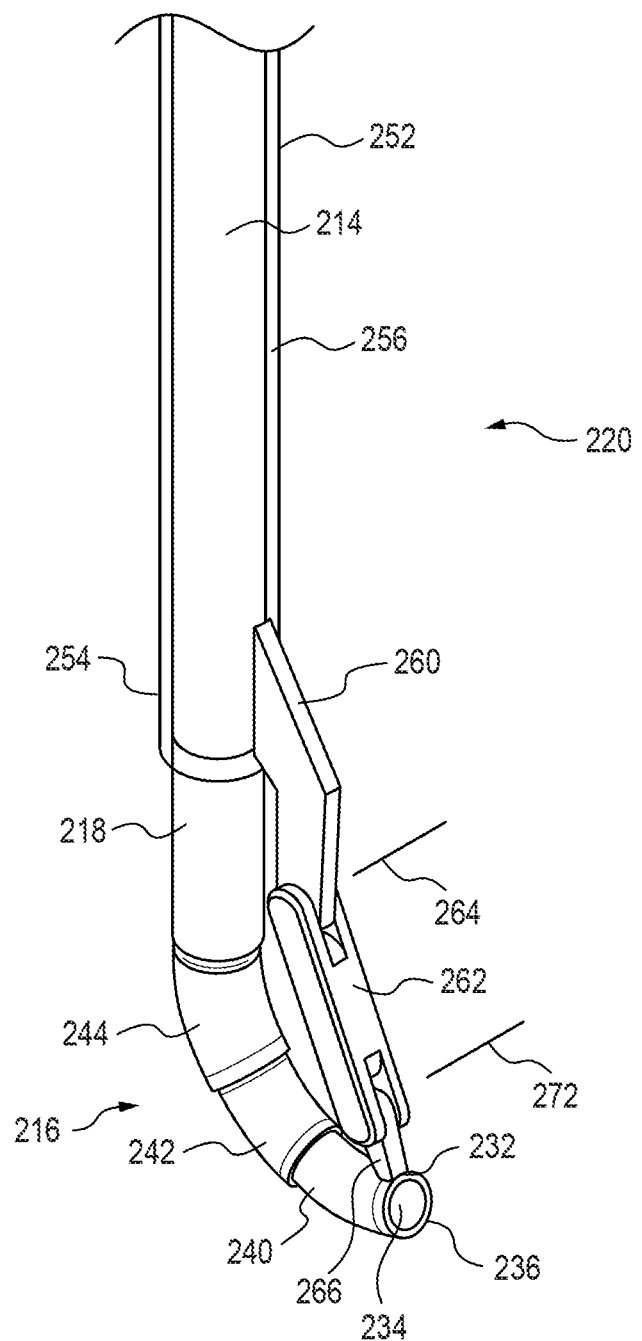
FIG. 8 is a perspective view of the distal end portion of the suturing device with the needle holder extended and the distal opening positioning mechanism in a second operating state.

FIGS. 7 and 8 depict a distal end portion of a suturing device 210 that is similar to the suturing device 10 depicted in FIGS. 1-4, however, the suturing device 210 depicted in FIGS. 7 and 8 includes an alternative needle holder 216 and an alternative distal opening positioning mechanism 220. The distal opening positioning mechanism 220 is shown in a first operating state in FIG. 7 and in a second operating state in FIG. 8. The suturing device 210 depicted in FIGS. 7 and 8 includes an actuator similar to the actuator described above, an elongate body 214, which is also similar to the elongate body 14 described with reference to FIGS. 1-4, and the needle holder 216. The actuator and the elongate body 214 have been described above.

The needle holder 216 extends away from a distal end portion 218 of the elongate body 214. The needle holder 216 is a telescopic assembly having a distal-most tip 232, a needle passage 234, and a distal opening 236. A needle (not shown) but similar to the needle 20 described above, is received in the needle passage 234 along with the suture, which is similar to the suture 22 depicted in FIG. 4. The needle holder 216 does not include a notch, however, a notch, which could be similar in configuration to the notch 140 (described above) could be provided to allow the needle holder 216 to operate in a similar manner to the needle holder 16 described above when the needle holder 16 is its pre-deformed shape.

The needle holder 216 includes a distal section 240, a medial section 242, and a proximal section 244. When the needle holder 216 is in an extended position, which occurs then the distal opening positioning mechanism 220 is in the second operating state (see FIG. 8), the medial section 242 is positioned between the distal section 240, which has the distal opening 236, and the proximal section 244. The proximal section 244 is adjacent to the elongate body 214.

The distal opening positioning mechanism 220 depicted in FIGS. 7 and 8 includes a moveable element, which can be a sleeve 252 similar to the sleeve 102, connected with and moveable with respect to the elongate body 214 and also connected with the needle holder 216 in a manner that will be described in more detail below. The sleeve 252 includes a distal end portion 254 positioned adjacent to the needle holder 216. The sleeve 252 depicted in FIGS. 7 and 8 is tubular and hollow to define a sleeve passage 256 that receives the elongate body 214 to allow the sleeve 252 to connect with the elongate body 214. A flange (not shown) that is similar to the flange 108 can be provided at a proximal end of the sleeve 252 to provide a manipulatable element configured to be manipulated by a human hand to move the sleeve 252 with respect to the elongate body 214. Like the sleeve 102 described above, the sleeve 252 as depicted is hollow between the flange and the distal end portion 254, however, the sleeve 252 can take other configurations, e.g., U-shaped or fully surrounding the elongate body 214 along only a portion of the elongate member.

A first linkage mount 260 extends from the distal end portion 254 of the sleeve 252. The first linkage mount 260 is pivotally connected with a linkage 262 to allow for the linkage 262 to pivot about a first axis 264 with respect to the first linkage mount 260. A second linkage mount 266 extends from the distal-most tip 232 of the needle holder 216 and pivotally connects with the linkage 262. As such, the linkage 262 can pivot with respect to the second linkage mount 266 about a second axis 272.

The sleeve 252 is moveable with respect to the elongate body 214 to change the operating state of distal opening positioning mechanism 220, e.g., between a first operating state and a second operating state. Upward (per the orientation of FIGS. 7 and 8) movement of the sleeve 252 with respect to the elongate body 214 retracts the needle holder 216 into or toward the elongate body 214. Downward (per the orientation of FIGS. 7 and 8) movement of the sleeve 252 with respect to the elongate body 214 extends the needle holder 216 away from the elongate body 214. As such, the distal opening positioning mechanism 220 is operable in different operating states to move the distal opening 236 with respect to the elongate body 214.

The distal section 240 is received inside the proximal section 244 when the distal opening positioning mechanism 220 is in the first operating state, which is shown in FIG. 7. The distal section 240 is not received inside the proximal section 244 when the distal opening positioning mechanism 220 is in the second operating state (see FIG. 8), which results from movement of the sleeve 252 with respect to the elongate body 214. Also, the medial section 242 is received inside the proximal section 244 and the distal section 240 is received inside the medial section 242 when the distal opening positioning mechanism 220 is in the first operating state. Also, the distal section 240 is not received inside the medial section 242 when the distal opening positioning mechanism 220 is in the second operating state.

Figure 9:
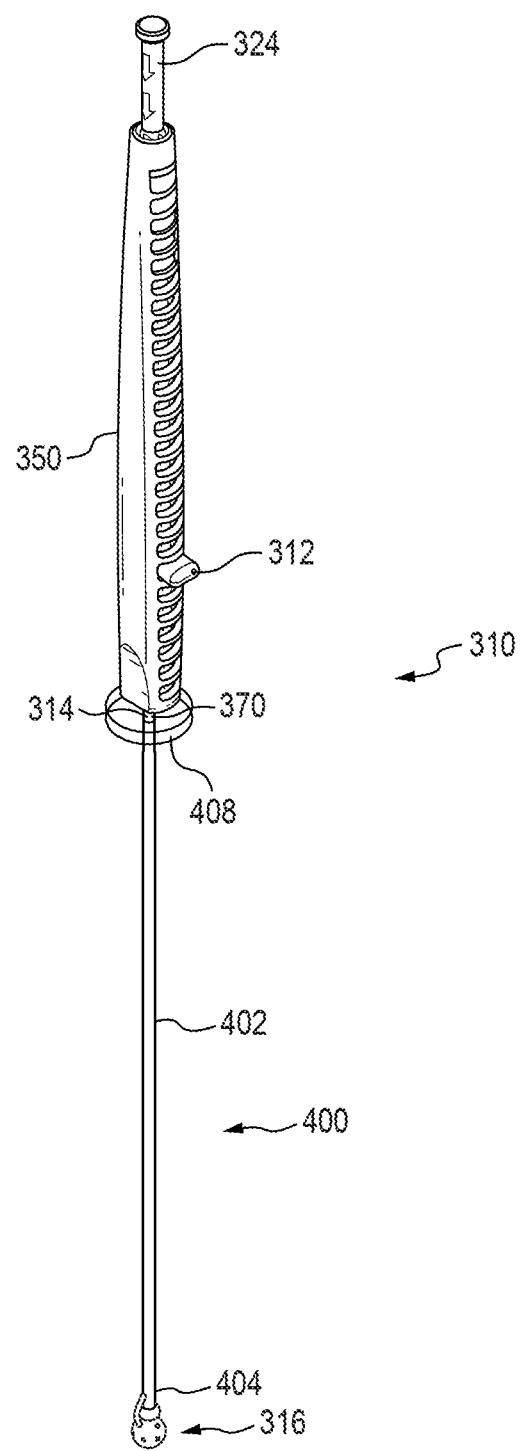
FIG. 9 is a perspective view of a suturing device including an alternative needle holder having a distal opening and another alternative distal opening positioning mechanism.
Figure 10:
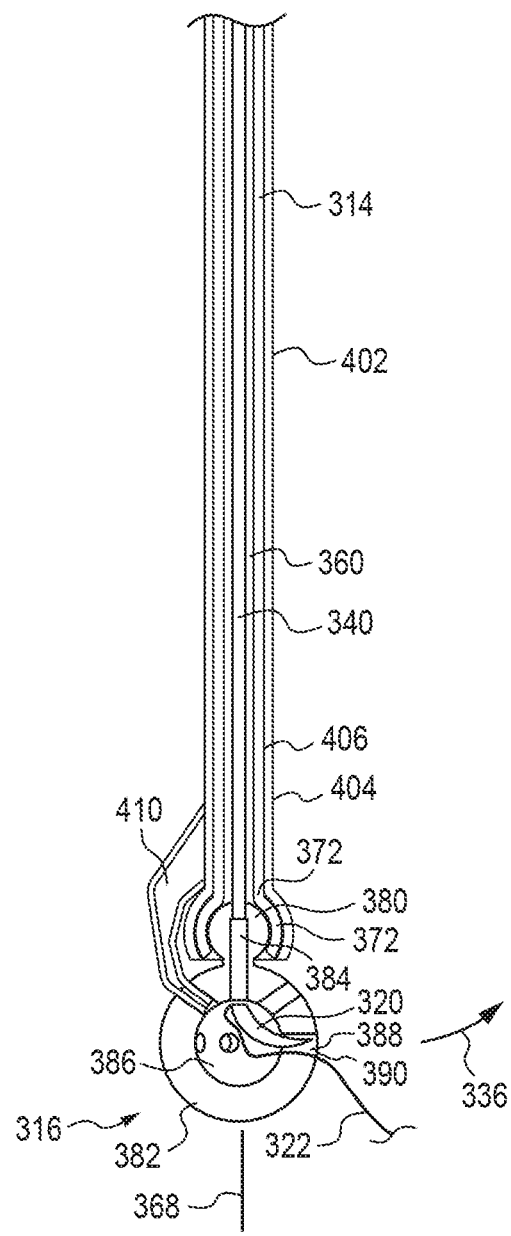
FIG. 10 is a cross-sectional view of a distal end portion of the suturing device depicted in FIG. 9.

FIG. 9 depicts another example of a suturing device 310. The suturing device 310 generally includes an actuator having a button 312, an elongate body 314, and a needle holder 316. The suturing device 310 is useful to accurately locate a needle 320 and a suture 322, which are shown in FIG. 10, to facilitate passing the needle 320 through target tissue to be sutured.

The needle 320 in the illustrated embodiment is similar to the needle 20 described above. The actuator, which includes the button 312 and a plunger 324, is more particularly described in U.S. application Ser. No. 15/654,878. Actuation of the actuator moves the needle 320 in an advance direction 336 with respect to the needle holder 316. The needle 320 moves from a retracted position, which is shown in FIG. 10, to a released condition in which the needle 320 is released from the needle holder 316. The suture 322 connects with the needle 320 and extends from the second end of the needle 320.

Movement of the actuator from a first operating position toward a second operating position moves the needle 320 in the advance direction 336 with respect to the needle holder 316 thus moving the needle 320 toward the released condition in which the needle 320 is released from the needle holder 316. In the illustrated embodiment, the actuator includes a flexible section, which in the illustrated embodiment is made up of a wire 340, which can be made from nitinol. The other components of the actuator are described in more detail in U.S. application Ser. No. 15/654878 and will not be described herein for the sake of brevity.

The elongate body 314 connects with a handle 350 in the illustrated embodiment. The elongate body 314 in the illustrated embodiment is in the form of a cannula. The elongate body 314 defines a track 360 that receives a portion of the actuator, more particularly the wire 340 in the illustrated embodiment. As described above, the elongate body 314 is a cannula and the track 360 is a lumen that receives the wire 340 of the actuator. The track need not encircle the wire 340, but could be U-shaped. In the depicted embodiments, the elongate body 314 is circular in a cross section taken normal to the longest dimension of the elongate body 314.

The elongate body 314 extends straight along a longitudinal axis 368 in the illustrated embodiment; however, the elongate body 314 could take alternative configurations, such as a bayonet configuration. The elongate body 314 includes the proximal end portion 370 and a distal end portion 372. The proximal end portion 370 connects with the handle 350. In the illustrated embodiment, the needle holder 316 is received in and connected with the elongate body 314 and extends away from the distal end portion 372. More particularly, the elongate body 314 includes a socket 374 at the distal end portion 372 for connecting with the needle holder 316, which will be described in more detail below. The elongate body 314 is made from a rigid metal material; however, if desired at least a portion of the elongate body 314 may be made from a malleable or flexible material to allow the surgeon to bend at least a portion of the elongate body 314 into a desirable configuration for insertion into an animal body during a surgical procedure. In the illustrated embodiment, an outer diameter of the elongate body 314 is constant between the proximal end portion 370 and the distal end portion 372. The outer diameter can be less than 3.5 mm, which provides a very slim device to enhance the line of sight for a surgeon during the surgical procedure.

The proximal end portion 370 of the elongate body 314 is received in the handle 350. The elongate body 314 and the needle holder 316 can rotatable with respect to the handle 350 about a rotational axis, which in the illustrated embodiment is coaxial with the longitudinal axis 368; however, rotation of the elongate body 314 and the needle holder 316 with respect to the handle 350 requires a greater amount of force to be applied on the elongate body 314 than the force that is typically applied to the elongate body 314 or the needle holder 316 while a surgeon is using the suturing device 310 during a suturing procedure.

The needle holder 316 extends away from the distal end portion 372 of the elongate body 314. In the embodiment illustrated in FIGS. 9 and 10, the needle holder 316 includes a hollow proximal spherical, or ball-shaped, section 380 and a hollow distal spherical, or ball-shaped, section 382. The proximal spherical section 380 is received inside the socket 374 to connect the needle holder 316 with the elongate body 314. The proximal spherical section 380 includes a passage 384 that can receive the wire 340 to allow the wire 340 to pass through the passage 384 and contact the needle 320.

With reference to FIG. 10, the distal spherical section 382 defines a needle cavity 386 and a needle passage 388 that are in communication with the track 360 of the elongate body 314 via the passage 384 in the proximal spherical section 380. The needle passage 388 opens to ambient through a distal opening 390. The distal opening 390 is offset from the longitudinal axis 368. At least a portion of the suture 322 extends along the needle passage 388 from the second end of the needle 320 toward the distal opening 390 between the needle 320 and an inner surface of the needle passage 388 when the needle 320 is received in the needle cavity 386 and the needle passage 388 and the actuator is in the first operating position. The maximum diameter of the distal spherical section 382 is less than 7 mm.

The needle holder 316 is configured to move with respect to the elongate body 314 to change the location of the distal opening 390 with respect to the elongate body 314. The suturing device 310 includes a distal opening positioning mechanism 400 operatively connected with the needle holder 316 and operable in different operating states to move the distal opening 390 with respect to the elongate body 314.

With reference to FIG. 9, the distal opening positioning mechanism 400 includes a movable element, which is a sleeve 402 in FIG. 9, connected with and movable with respect to the elongate body 314 and also connected with the needle holder 316. A distal end portion 404 of the sleeve 402 is positioned adjacent the needle holder 316. The sleeve 402 depicted in FIGS. 9 and 10 is tubular and hollow to define a sleeve passage 406 (FIG. 10) from the distal end portion 404 to a flange 408 extending outwardly from the sleeve 402 located at or adjacent a proximal end of the sleeve 402. The flange 408 is an example of a manipulatable element provided on the sleeve 402 that is configured to be manipulated by a human hand to move the sleeve 402 with respect to the elongate body 314. The sleeve 402 is depicted as hollow between the flange 408 and the distal end portion 404, however, it can take other configurations, e.g. U-shaped or fully surrounding the elongate body 314 along only a portion of elongate body 314 to allow for the sleeve 402 to connect with the elongate body 314.

The sleeve 402 is rotatable around the longitudinal axis 368 and with respect to the elongate body 314. The needle holder 316 is rotatable also rotatable around the longitudinal axis 368 and with respect to the elongate body 314. The distal opening positioning mechanism 400 includes an arm 410 extending from the distal end portion 404 of the sleeve 402. The arm 410 contacts the distal spherical section 382 and applies a force to the distal spherical section 382 such that rotation of the sleeve 402 with respect to the elongate body 314, e.g. by the surgeon manipulating the flange 408, results in rotation of the needle holder 316 with respect to the elongate body 314.

Figure 11:
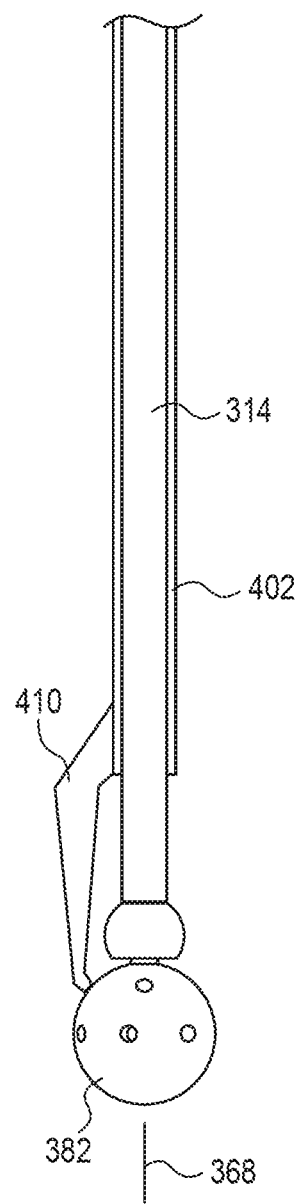
FIG. 11 is a side view of a distal end portion of a suturing device slightly modified from the suturing device depicted in FIG. 9.

FIG. 11 shows a modification where the sleeve 402 is rotatable around the longitudinal axis 368 and with respect to the elongate body 314 and also slidable along the longitudinal axis 368 and with respect to the elongate body 314. In this modification, the arm 410 contacts the distal spherical section 382 and applies a force to the distal spherical section 382 such that rotation of the sleeve 402 with respect to the elongate body 314 results in rotation of the needle holder 316 with respect to the elongate body 314. Also, the needle holder 316 is pivotable with respect to the elongate body 314 about at least two perpendicular axes, which are both perpendicular to the longitudinal axis 368. The sleeve 402 can slide along the elongate body 314 (and along the longitudinal axis 368) which results in movement of the arm 410. With the proximal spherical section 380 being received inside the socket 374 (FIG. 10), the distal spherical section 382 is able to pivot about multiple axes that are each perpendicular to the longitudinal axis 368 as the sleeve 402 slides along the elongate body 314.

Figure 12:
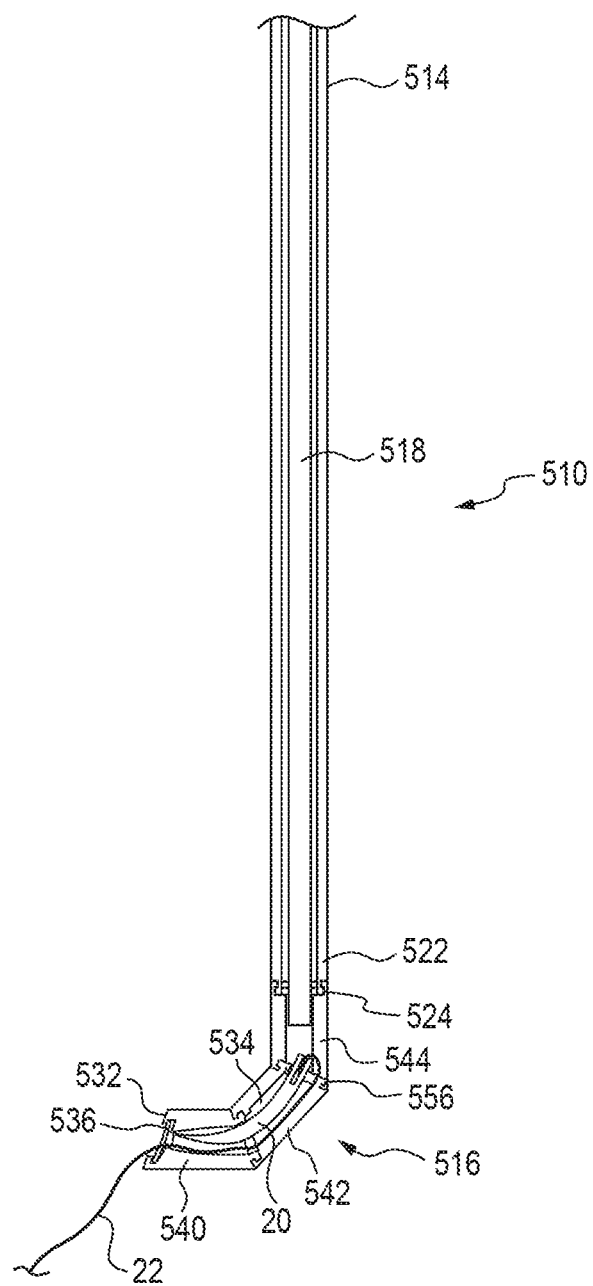
FIG. 12 is a cross-sectional view of a distal end portion of a suturing device including another alternative needle holder having a distal opening.
Figure 13:
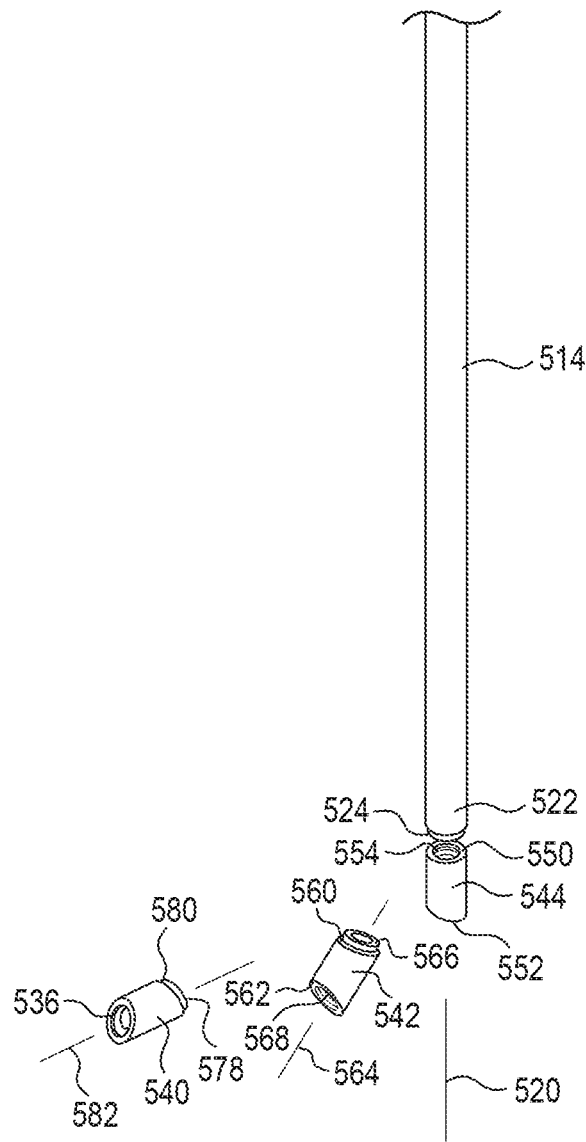
FIG. 13 is an exploded view of the distal end portion of the suturing device depicted in FIG. 12.

FIGS. 12 and 13 depict a distal end portion of a suturing device 510 that is similar to the suturing device 10 depicted in FIGS. 1-4, however, the suturing device 510 depicted in FIGS. 12 and 13 includes an alternative needle holder 516. The suturing device 510 includes an actuator similar to the actuator described above, an elongate body 514, which is also similar to the elongate body 14 described with reference to FIGS. 1-4, and the needle holder 516. The actuator, which can include a wire 518 similar to the wire 40 described above, and the elongate body 514 have been described above. The lower portion of the elongate body 514 is coaxial with a longitudinal axis 520.

The needle holder 516 extends away from a distal end portion 522 of the elongate body 514. The elongate body 514 differs from the elongate body described above in that the elongate body includes a collar 524 extending in a distal direction from the distal end portion 522. The needle holder 516 includes a distal-most tip 532, a needle passage 534, and a distal opening 536. The needle 20 is received in the needle passage 534 along with the suture 22. The needle holder 516 does not include a notch, however, a notch, which could be similar in configuration to the notch 140 (described above), could be provided to allow the needle holder 516 to operate in a similar manner to the needle holder 16 described above when the needle holder 16 is its pre-deformed shape. The needle holder 516 includes a distal section 540, a medial section 542, and a proximal section 544. The medial section 542 is positioned between the distal section 540, which has the distal opening 536, and the proximal section 544. The proximal section 544 is adjacent to and connects with the elongate body 514.

The needle holder 516 is configured to move with respect to the elongate body 514 to change the location of the distal opening 536 with respect to the elongate body 514. With reference to FIG. 13, the proximal section 544 includes a proximal end surface 550 that is normal to the longitudinal axis 520 and a distal end surface 552 that is inclined with respect to the longitudinal axis 520. The proximal section 544 also includes a proximal channel 554 that is annular and receives the collar 524 to connect the proximal section 544 with the elongate body 514. The proximal section 544 also includes a distal channel 556 (see FIG. 12) that allows for connection between the proximal section 544 and the medial section 542. The medial section 542 includes a proximal end surface 560 and a distal end surface 562 that are each inclined with respect to a central axis 564 of the medial section 542. The incline angle of the proximal end surface 560 of the medial section 542 with respect to the central axis 564 of the medial section 542 matches the incline angle of the distal end surface 552 of the proximal section 544 with respect to the longitudinal axis 520. The medial section 542 includes a proximal collar 566 that is received in the distal channel 556 of the proximal section 544 to connect the medial section 542 with the proximal section 544. The medial section 542 also includes a distal channel 568 that allows for connection between the medial section 542 and the distal section 540. The distal section 540 includes a proximal end surface 580 that is inclined with respect to a central axis 582 of the distal section 540. The incline angle of the proximal end surface 580 of the distal section 540 with respect to the central axis 582 of the distal section 540 matches the incline angle of the distal end surface 562 of the medial section 542 with respect to the central axis 564 of the medial section 542. The distal section 540 also includes a proximal collar 578 that is received in the distal channel 568 of the medial section 542 to connect the medial section 542 with the distal section 540.

The needle holder 516 is configured to move with respect to the elongate body 514 to change the location of the distal opening 536 with respect to the elongate body 514. The distal section 540 can be rotated about the central axis 582 of the distal section 540 with respect to the medial section 542. The proximal end surface 580 of the distal section 540 rides along the distal end surface 562 of the medial section 542. Because of the incline of the proximal end surface 580 of the distal section 540 with respect to the central axis 582 of the distal section 540, the location of the distal opening 536 with respect to the elongate body 514 can be changed. Similarly, the medial section 542 can be rotated about the central axis 564 of the medial section 542 with respect to the proximal section 544 and the distal section 540. Because of the incline of the proximal end surface 560 of the medial section 542 with respect to the central axis 564 of the medial section 542 and the incline of the distal end surface 566 of the medial section 542 with respect to the central axis 564 of the medial section 542, the location of the distal opening 536 with respect to the elongate body 514 can be changed. Also, the proximal section 544 can be rotated with respect to the elongate body 514 about the longitudinal axis 520 to change the location of the distal opening 536 with respect to the elongate body 514. Accordingly, each section 540, 542, 544 includes a cam surface cooperating with an adjacent section such that rotation of one of the sections with respect to an adjacent section results in rotation of the adjacent section with respect to the section being rotated.

Suturing devices have been described above with particularity. Modifications and alterations will occur to those upon reading and understanding the above detailed description. The invention, however, is not limited to only the embodiments described above. Instead, the invention is broadly defined by the appended claims and the equivalents thereof. Also, as used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:
   an elongate body including a proximal end portion and a distal end portion;
   an actuator interacting with the elongate body and operable between a first operating position and a second operating position;
   a needle including a first end, which is pointed, and a second end, which is opposite the first end, and a suture connected with the needle, wherein the actuator is configured such that movement of the actuator from the first operating position toward the second operating position moves the needle in an advance direction, wherein the needle is positioned in the needle passage when the actuator is in the first operating position and the needle passes through the distal opening when moving in the advance direction;
   a distal opening positioning mechanism operatively connected with the needle holder, the distal opening positioning mechanism being operable in different operating states to move the distal opening with respect to the elongate body, wherein the distal opening positioning mechanism includes a sleeve connected with and movable with respect to the elongate body and also connected with the needle holder;
   wherein the sleeve at least partially surrounds the needle holder having a sleeve distal end positioned adjacent the distal opening when the distal opening positioning mechanism is in a first operating state prior to moving the distal opening with respect to the elongate body;
   wherein the needle holder is made from a shape memory material that returns to a pre-deformed shape after a force has been removed and the sleeve provides the force on the needle holder such that the needle holder takes a deformed shape when the distal opening positioning mechanism is in the first operating state.

2. The suturing device of claim 1, wherein the sleeve fully surrounds the elongate body.

3. The suturing device of claim 1, wherein the sleeve includes a manipulatable element configured to be manipulated by a human hand to move the sleeve with respect to the elongate body.

4. The suturing device of claim 3, wherein the manipulatable element is a flange extending outwardly from the sleeve located at or adjacent a proximal end of the sleeve.

5. The suturing device of claim 1, wherein the sleeve at least partially surrounds the elongate body having a sleeve distal end portion positioned adjacent the needle holder when the distal opening positioning mechanism is in a first operating state prior to moving the distal opening with respect to the elongate body.

6. A suturing device comprising:
   an elongate body including a proximal end portion and a distal end portion;
   an actuator interacting with the elongate body and operable between a first operating position and a second operating position;
   a needle holder extending away from the distal end portion or provided as part of the distal end portion of the elongate body, the needle holder defining a needle passage and a distal opening, wherein the needle holder is made from a shape memory material that returns to a pre-deformed shape after a force has been removed;
   a needle received in the needle passage, wherein the actuator is configured such that movement of the actuator from the first operating position toward the second operating position moves the needle in an advance direction; and
   a sleeve at least partially surrounding the needle holder having a sleeve distal end positioned adjacent the distal opening when the distal opening positioning mechanism is in a first operating state prior to moving the distal opening with respect to the elongate body, and the sleeve provides the force on the needle holder such that the needle holder takes a deformed shape when the distal opening positioning mechanism is in the first operating state.

\* \* \* \* \*